United States Patent [19]

Atwood

[11] 4,024,170

[45] May 17, 1977

[54] LIQUID CLATHRATES

[75] Inventor: Jerry L. Atwood, Tuscaloosa, Ala.

[73] Assignee: University of Alabama, University, Ala.

[22] Filed: Nov. 11, 1975

[21] Appl. No.: 630,912

[52] U.S. Cl. .................. 260/438.5 R; 208/322; 260/429 AR; 260/439 CY; 260/448 A; 260/666 SA

[51] Int. Cl.² ...................................... C07F 11/00

[58] Field of Search ... 260/448 A, 429 AR, 439 CY, 260/438.5 R, 674 R; 208/322

[56] References Cited

UNITED STATES PATENTS

| | | | |
|---|---|---|---|
| 2,844,615 | 7/1958 | Ziegler et al. | 260/448 A |
| 2,872,470 | 2/1959 | Reed et al. | 260/448 A |
| 3,101,360 | 8/1963 | Parts | 260/429 AR |
| 3,231,593 | 1/1966 | Hafner et al. | 260/429 AR |
| 3,280,025 | 10/1966 | Poe et al. | 208/322 |
| 3,711,529 | 1/1973 | Shepherd | 260/448 A |

*Primary Examiner*—Helen M. S. Sneed
*Attorney, Agent, or Firm*—Oblon, Fisher, Spivak, McClelland & Maier

[57] ABSTRACT

Liquid clathrates of the formula:

$M\{Al_2[CH_2]_xCH_3]_6NO_3\}\cdot n\ Y$, wherein M is potassium, rubidium, cesium, tetraalkylammonium, tetraarylammonium, tetraalkylphosphonium or tetraarylphosphonium, $x$ is an integer from 1 to 3 and Y is an aromatic compound.

5 Claims, No Drawings

LIQUID CLATHRATES

BACKGROUND OF THE INVENTION

1. Field of the Invention

The present invention relates to complexes of certain aromatic hydrocarbons and metal salts. More particularly, the present invention relates to liquid clathrates of small aromatic hydrocarbons and metal salts formed by the combination of an alkali metal, ammonium or the like nitrate with a trialkyl aluminum compound wherein the liquid clathrate is immiscible in the neat aromatic hydrocarbon.

2. Description of the Prior Art

Liquid clathrates of small ring aromatic compounds and complex metal salts formed by the reaction of simple alkali metal or ammonium salts with trimethylaluminum in a mole ratio of 1:2 are known as described in a series of publications authored by J. L. Atwood et al in the Journal of Organometallic Chemistry (Vol. 66, pp. 15–21 (1974); Vol. 42, pp. C77–79 (1972); Vol. 61, pp. 43–48 (1973); and Vol. 65, pp. 145–154 (1974)). The complex metal salts which form the liquid clathrates with certain aromatic solvents are prepared by reacting simple salts such as the alkali metal or ammonium halides, azides, thiocyanates and selenocyanates with trimethylaluminum in appropriate amounts such that salts of the stoichiometry, $M[Al_2(CH_3)_6X]$ are formed. When the complex metal salts are treated with certain aromatic compounds such as benzene or toluene, liquid complexes or clathrates form which contain at least two and up to about 13 aromatic molecules per complex salt molecule. The liquid clathrates can be distinguished from the rest of the particular aromatic hydrocarbon solvent to which the complex metal salt is exposed by the formation of a second liquid layer which is immiscible with the hydrocarbon solvent.

Despite the fact that the trimethylaluminum-simple salt complexes form liquid clathrates, no examples are known of complex salts containing trialkylaluminum moieties wherein the alkyl groups are greater than methyl, which form liquid clathrates. Furthermore, it would be desirable to possess complexes which form clathrates with more than 13 aromatic molecules per molecule of complex and which form clathrates with aromatic molecules such as naphthalene, anthracene, phenanthrene, and the like sizes greater than the simple aromatic molecules.

A need therefore, continues to exist for trialkylaluminum-simple complexes which form liquid clathrates with relatively large numbers of relatively large aromatic molecules.

SUMMARY OF THE INVENTION

Accordingly, one object of the present invention is to provide a series of complex metal nitrate salts which form liquid clathrates with aromatic hydrocarbons.

Another object of the invention is to provide a series of liquid clathrates of complex metal salts formed by the combination of a trialkylaluminum of $C_{1-4}$ carbon atoms with a simple salt in a mole ratio of 2:1.

Briefly, these objects and other objects of the present invention as hereinafter will become more readily apparent can be attained by liquid clathrates of an aromatic hydrocarbon and a complex metal nitrate salt of the formula:

$$M\{Al_2[(CH_2)_x-CH_3]_6NO_3\}$$

wherein M is potassium, rubidium, cesium, tetraalkylammonium, tetraarylammonium, tetraalkylphosphonium or tetraarylphosphonium and $x$ is an integer from 1–3.

DETAILED DESCRIPTION OF THE PREFERRED EMBODIMENTS

As set forth above, complex metal salts of a simple salt and trimethylaluminum having the formula $M[Al_2(CH_3)_6X]$ are known to form liquid clathrates with simple aromatic molecules such as toluene, xylene, benzene and the like, wherein from 1.5 to about 13 aromatic molecules combine with a mole of complex metal salt. The unique ability of these trimethylaluminum containing compounds to form liquid clathrates with aromatic molecules is believed to result from the structure of the complex salt molecules which is believed to be angular as shown in structure

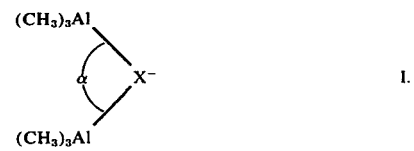

There are two important features of the angular structure. First, the complex anion has an appreciable dipole moment and second, there is a definite separation of inorganic and organic regions of the molecule. Consequently, the negative charge in the anion is substantially located on the very accessible inorganic region of the anion, while the relatively large organic portion of the anion is located further away.

Those anions whose geometry is essentially linear, i.e., where $\alpha = 180°$, have been found not to possess the ability to form liquid clathrates. An example of such an anion is the fluoride anion, $[Al_2(CH_3)_6 F]^-$. The evidence above suggests that as the anion passes from an angular configuration to an essentially linear configuration, the ability of the anion to form liquid clathrates should decrease and eventually be lost. Furthermore, as the size of the alkyl substitution increases on the aluminum atoms, it would follow that steric interaction and repulsion would result, thereby forcing the anion to assume a more linear configuration as the angle alpha increases. This hypothesis would seem to be substantiated by the experimental observation that when the size of the alkyl substitution is increased to ethyl or greater, the anions lose their ability to form liquid clathrates. Although, this has only been substantiated for azide and thiocyanate complexes.

It has now been discovered that nitrate ion containing complex salts have the ability to complex with aromatic molecules to form liquid clathrates, when the size of the alkyl substitution on the aluminum atom is greater than methyl. In other words, complex salts having the formula $$M\{Al_2[(CH_2)_x CH_3]_6 NO_3\},$$

wherein M is rubidium, cesium, potassium, tetraaryl-or tetraalkylammonium or tetraaryl-or tetraalkylphosphonium, and $x$ is 1–3, successfully form liquid clathrates with simple aromatic molecules. The size of the aryl and alkyl groups in the ammonium and phosphonium cations is not critical. In fact, as the alkyl and aryl groups become larger, a greater number of aromatic molecules can be added to the clathrate. However, eventually a point is reached at which the clathrates become an ordinary solution which is undesirable. Therefore, a balance must be maintained between the need for clathrates containing large numbers of aromatic molecules and the need for a strong clathrate which maintains its integrity as a clathrate. Suitable examples of ammonium and phosphonium cations which provide strong clathrates include tetramethylammonium, tetraethylammonium, tetrapropylammonium, methyltriphenylammonium and tetraphenylphosphonium. Suitable aromatic compounds include benzene, toluene, o-, m- and p-xylene, mesitylene, tetramethylbenzene, ethylbenzene, diethylbenzene, cumeme, trimethylbenzene, dipropylbenzene, diisopropylbenzene, naphthalene, tetralin, anthracene, phenathrene and small organometallic molecules such as trimethylaluminum, ferrocene, and dibenzenechromium. Small amounts of such non-aromatic hydrocarbons as cyclohexane can also be incorporated in the clathrates. It must be emphasized that clathrates will not form with the non-aromatic hydrocarbon per se. The clathrate of an aromatic compound will form first and thereafter, the non-aromatic hydrocarbon molecule will be incorporated in the clathrate. The complex nitrate anion of the present invention complexes with from 1.5 to about 30 aromatic molecules per molecule of complex anion.

The reason why the nitrate containing anions possess the unique ability to form liquid clathrates with a variety of alkyl substitution on aluminum is believed to be a consequence of the shape of the anion as follows:

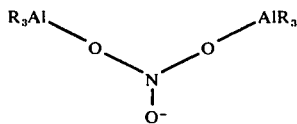

It is apparent from the above structure that the bridging nitrate group maintains the aluminum atoms apart at a greater distance which permits greater steric bulk on the aluminum atoms while at the same time preserving the angular configuration of the anion. Consequently, a series of complex anions is provided which contain alkyl groups of methyl and greater which form liquid clathrates. The clathrates of the nitrate containing anions also have the characteristic that when a trialkylaluminum compound is added in even the slightest excessive amounts over the 2:1 stoichiometry of the complex anion, the color of the clathrate turns from colorless to yellow. Presumably, the color shift is caused by a shift in energy of an electronic transition on the $NO_3^-$ ion by coordination of the excess trialkylaluminum molecule.

In the present invention, the term "liquid clathrate" describes the non-stoichiometric interaction of aromatic molecules with the complex nitrate anion, normally in amounts of 1.5 to about 30 aromatic molecules per complex nitrate anion. The interaction of the anion with the aromatic liquid results in a liquid clathrate which is immiscible with the neat aromatic compound. The aromatic molecules are approximately trapped in the clathrates much as they would be in a solid clathrate. The clathrates are freed or destroyed by lowering the temperature and the liberated aromatic molecules can be recovered. The interaction of aromatic molecules and complex anion can be summarized by the following equilibrium.

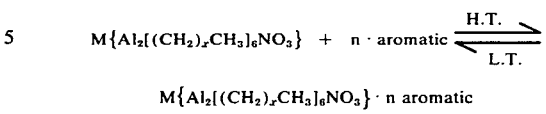

$$M\{Al_2[(CH_2)_xCH_3]_6NO_3\} \cdot n \text{ aromatic}$$

The clathrates are generally stable at temperatures up to about 120° C. The stability of the clathrates is rather insensitive to the nature of the cation.

In the preparation of the complex nitrate containing salt a suitable nitrate salt containing one of the appropriate cation species mentioned above is combined with a trialkylaluminum compound in a mole ratio sufficient to achieve a complex which is usually 1 to 2 in the presence of an aromatic solvent in the absence of oxygen or water. The reaction begins slowly at room temperature and can be heated to a temperature as high as 80° C, preferably no more than 40° C to complete the reaction. The clear, crystalline complex salt is then obtained. The complex salt can simply be recovered from the clathrate by lowering the temperature.

In the preparation of a liquid clathrate a suitably prepared complex nitrate salt is combined with an aromatic compound and heated to a temperature of a maximum of about 110° C. Upon cooling to room temperature, the liquid clathrate will remain for an indefinite period of time.

The nitrate anion clathrates decompose by two possible reactions.

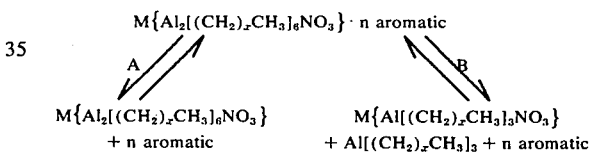

Both $K[Al_2(CH_3)_6NO_3] \cdot n$ aromatic and $Cs[Al_2(CH_3)_6NO_3] \cdot n$ aromatic are unstable with respect to conversion by route A. The nature of the aromatic compound complex is also an important factor in the mode of decomposition. For example, the liquid clathrate of n-propylbenzene with $Rb[Al_2(CH_3)_6NO_3]$ does not exist at room temperature. However, the clathrate of the same complex salt with ethylbenzene has low stability at room temperature, while the clathrate with benzene at room temperature is quite stable. Therefore, just as the formation of the parent nitrate molecule $M[Al_2R_6NO_3]$ is primarily determined by a series of lattice energy considerations, so is the stability of the liquid clathrate.

The ability of the present liquid clathrate to undergo exchange reactions of the guest aromatic molecule with another aromatic molecule is of primary importance. For instance, as a non-limiting example of an exchange reaction, $[Et_4N][Al_2(CH_3)_6NO_3]$ when mixed with a 1:1 mole ratio of benzene:toluene forms a liquid clathrate containing 1.02 moles benzene per 0.98 moles toluene. If the complex salt is mixed with a 1:1 mole ratio of benzene-mesitylene, the clathrate which forms contains two moles of benzene per one mole of mesitylene. In another example, the combination of the same tetraethylammonium salt above with a 1:1 mole ratio of benzene-cyclohexane forms a clathrate containing two moles of benzene per mole of cyclohexane.

It is apparent from the above discussion that the utility of the present complex nitrate salts is the ability of the complex salts to separate aromatic compounds as well as to separate aromatic compounds from other aromatic compounds.

The infrared spectra of all of the liquid clathrates formed from benzene are quite familiar. The spectra, however, reveal two significant differences between benzene entrapped within the liquid clathrate and neat benzene: the combination bands of benzene at 1818cm$^{-1}$ and 1962cm$^{-1}$ are broadened, and a very weak peak appears to 990cm$^{-1}$. The data is Table 1 below for a series of clathrates related to the present nitrate clathrates show broadening of the infrared bands at 1818cm$^{-1}$ and 1962 cm$^{-1}$ and is a measure of the extent of the interaction of the cation of the complex salt with the benzene molecules. The data for the Rb$^+$ and Cs$^+$ containing complex salts show a splitting of the degenerate peaks, while the relatively larger ammonium ions (relative to Cs$^+$ and Rb$^+$) for the remaining salts only broaden the peaks. Within the tetraalkylammonium series, the broadening tendency is shown, and the anticipated reduction of the broadening at increased Ar/An ratios can be observed for the tetra-n-pentylammonium clathrates.

The fact that this is the only mode which is affected by the formation of the benzene clathrate is an indication that the interaction of the anionic center with the benzene nucleus is localized over the carbon-carbon bonds of benzene rather than symmetrically centered in the $\pi$ system of benzene.

Further insight to the molecular arrangement of the constituents of the liquid clathrates has been obtained from a study of the X-ray diffraction data of the compound:

K[CH$_3$Se{Al(CH$_3$)$_3$}$_3$]. 2 C$_6$H$_6$, which is obtained by the thermal decomposition of the parent benzene liquid clathrate. This particular compound represents the particular situation where the proper combination of cation, anion and guest aromatic compound results in a material which is liquid at slightly elevated temperatures, but is solid at room temperatures. This property of the selenium compound is just opposite to the property of Cs[Al(CH$_3$)$_6$NO$_3$] . benzene, for instance,

Table I

Infrared Data on Selected Liquid Clathrates (10)

| Clathrate | Band Width$^a$ (1818 cm$^{-1}$) | Band Width (1962 cm$^{-1}$) | Absorbance A (990 cm$^{-1}$) | Absorbance B (1035 cm$^{-1}$) | Ratio A/B |
|---|---|---|---|---|---|
| Rb[Al$_2$(CH$_3$)$_6$N$_3$]· 6.1 C$_6$H$_6$ | {1816, 1836}$^b$ | {1960, 1974}$^b$ | 0.029 | 0.448 | 0.065 |
| Cs[Al$_2$(CH$_3$)$_6$N$_3$]· 7.4 C$_6$H$_6$ | {1815, 1833}$^b$ | {1960, 1972}$^b$ | 0.036 | 0.650 | 0.055 |
| [N(CH$_3$)$_4$][Al$_2$(CH$_3$)$_6$I]· 6.5 C$_6$H$_6$ | 28 | 24 | 0.011 | 0.245 | 0.045 |
| [N(C$_2$H$_5$)$_4$][Al$_2$(CH$_3$)$_6$I]· 7.3 C$_6$H$_6$ | 28 | 25 | | | |
| [N(C$_4$H$_9$)$_4$][Al$_2$(CH$_3$)$_6$I]· 9.7 C$_6$H$_6$ | 27 | 25 | 0.014 | 0.271 | 0.052 |
| [N(C$_5$H$_{11}$)$_4$][Al$_2$(CH$_3$)$_6$I]· 11.0 C$_6$H$_6$ | 25 | 22 | 0.020 | 0.407 | 0.049 |
| [N(C$_5$H$_{11}$)$_4$][Al$_2$(CH$_3$)$_6$I]· 13.0 C$_6$H$_6$ | 24 | 18 | 0.014 | 0.234 | 0.060 |

$^a$Width at half-height in cm$^{-1}$.
$^b$Split into distinct peaks with maxima at wave numbers given in bracketts.
$^c$The 990 cm$^{-1}$ absorbance is obscured by a strong absorbance at 995 cm$^{-1}$ due to the N(C$_2$H$_5$)$_4$$^+$ groups.

The infrared spectrum of benzene has been thoroughly studied and the absorption peak at 1818cm$^{-1}$ is assigned to the combined $E_u^{++}$ $E_u^-$ fundamentals which have $E_u^-$symmetry. The band of benzene at 1962cm$^{-1}$ is also a combination band of the $B_{2g}$ and $E_u^+$ fundamentals having $E_u^-$ symmetry. The two factors of importance are that the combined bands each possess the $E_u^+$ fundamental, and that both bands are degenerate and can be broadened by partial lifting of the degeneracy. The $E_u^+$ fundamental is symmetry forbidden and it is not observed where its location is predicted at 970 – 985cm$^{-1}$, in the neat benzene spectrum. On the other hand, the spectra of the benzene containing clathrates show a very weak band at 990cm$^{-1}$. Since it appears in all of the benzene clathrates, its presence must be due either to the complexed benzene or to the trimethylaluminium units. The peak in question is correctly assigned to benzene because the correct absorbance ratios are observed based on the peak at 1035cm$^{-1}$, which is assigned to the $E_u^-$ fundamental of benzene. These ratios for a variety of compounds are shown in Table I above.

The $E_u^+$ mode can be illustrated as follows:

which is very unstable at 25° C, but completely stable at 80° C.

The noteworthy feature of the structure defined by the X-ray data is that, despite the fact the conventional agreement index R is 0.092 which means the structural problem is essentially solved, the benzene molecules of the clathrate (the benzene molecules comprise 35% of the total electron density) are not included in the structure defined. Moreover, it is not possible to accurately locate and refine the positional parameters of the atoms of the benzene molecules. These observations substantially suggest that the benzene molecules are not confined in rigid lattice positions, but behave substantially as a liquid.

Usually, the ratio of aromatic molecules per unit amount of complex anion ranges from 1.5 up to about 30. For each individual nitrate anion, however, the aromatic/anion ratio depends upon the following factors:

a. the larger the associated cation, the greater the number of aromatic molecules in the clathrate;

b. the larger the alkyl group bonded to the aluminum atom, the greater the number of aromatic molecules in the clathrate; and c. the larger the particular aromatic species, the less the number of aromatic molecules in the liquid clathrate.

Having generally described this invention, a further understanding can be obtained by reference to certain specific examples which are provided herein for purposes of illustration and are not intended to be limiting unless otherwise specified.

EXAMPLE 1

Preparation of M[Al$_2$(CH$_3$)$_6$NO$_3$], M = K, Rb or Cs

A 0.005 mole quantity of potassium, rubidium or cesium nitrate was placed in a reaction tube and transferred to a dry box. Benzene (0.04 mole) was added which prevents the reaction from becoming too vigorous. Thereafter, 0.010 mole of trimethylaluminium was added to the tube, and the reaction began slowly at room temperature. To complete the reaction the mixture was heated to 60° C, and a clear, crystalline complex salt was obtained in 100% yield after filtration.

A liquid clathrate of the complex salt obtained was prepared by combining all of the salt obtained above with 0.100 mole of benzene, and heating the mixture to 110° C. When cooled, the liquid clathrate was stable at room temperature.

EXAMPLE 2

Preparation of [(C$_2$H$_5$) N][Al$_2$(CH$_3$)$_6$NO$_3$]

A 0.005 mole quantity of tetraethylammonium nitrate was placed in a reaction tube and transferred to a dry box. Benzene (0.030 mole) was added and thereafter, 0.010 mole of trimethylaluminum was added to the mixture. The reaction started slowly and was completed by heating to 60° C. The clear, crystalline complex salt was obtained after filtration in 100% yield.

EXAMPLE 3

Preparation of [(C$_2$H$_5$)$_4$N][Al$_2$(C$_2$H$_5$)$_6$NO$_3$]

A 0.005 mole quantity of tetraethylammonium nitrate was placed in a reaction tube and transferred to a dry box. Benzene (0.030 mole) was added and thereafter, 0.010 mole triethylaluminum was added to the mixture. The reaction started slowly and was completed by heating to 60° C. The clear, crystalline complex salt was obtained after filtration in 100% yield.

Having now fully described this invention, it will be apparent to one of ordinary skill in the art that many changes and modifications can be made thereto without departing from the spirit or scope of the invention as set forth herein.

What is claimed as new and intended to be covered by letters patent is:

1. Complex nitrate salt containing molecules of the formula comprising:

$$M\{Al_2[(CH_2)_xCH_3]_6NO_3\}$$

wherein M is potassium, rubidium, cesium, tetraalkylammonium, tetraarylammonium, tetraalkylphosphonium or tetraarylphosphonium and $x$ is an integer from 1 to 3.

2. The complex salt of claim 1, wherein said tetraalkylammonium cation is tetramethylammonium, tetraethylammonium, tetrapropylammonium or methyltriphenylammonium.

3. The complex salt of claim 1, wherein said tetraarylphosphonium cation is tetraphenylphosphonium.

4. The complex salt of claim 1, wherein M is tetraethylammonium and $x$ is one.

5. Liquid clathrates of the formula:

$$M(Al_2[(CH_2)_xCH_3]_6NO_3) \cdot nY$$

wherein M and $x$ are as defined in Claim 1, $n$ is a value from 1.5 to 30 and Y is an aromatic compound selected from the group consisting of benzene, toluene, o-, m- and p-xylene, mesitylene, tetramethylbenzene, ethylbenzene, diethylbenzene, cumene, trimethylbenzene, dipropylbenzene, diisopropylbenzene, naphthalene, tetralin, anthracene, and phenanthrene; or an organometallic compound selected from the group consisting of trimethylaluminum, ferrocene and dibenzenechromium.

* * * * *